US008798701B2

(12) United States Patent
Izzetoglu et al.

(10) Patent No.: US 8,798,701 B2
(45) Date of Patent: Aug. 5, 2014

(54) FUNCTIONAL NEAR-INFRARED SPECTROSCOPY AS A MONITOR FOR DEPTH OF ANESTHESIA

(75) Inventors: Kurtulus Izzetoglu, Drexel Hill, PA (US); Kambiz Pourrezaei, Gladwynne, PA (US); Banu Onaral, Philadelphia, PA (US); Jay Charles Horrow, Wynnewood, PA (US); Meltem Alkan Izzetoglu, Drexel Hill, PA (US); Scott C. Bunce, Hummelstown, PA (US)

(73) Assignees: Drexel University, Philadelphia, PA (US); Philadelphia Health & Education Corporation, Philadelphia, PA (US)

( * ) Notice: Subject to any disclaimer, the term of this patent is extended or adjusted under 35 U.S.C. 154(b) by 1224 days.

(21) Appl. No.: 12/571,145

(22) Filed: Sep. 30, 2009

(65) Prior Publication Data
US 2010/0081903 A1   Apr. 1, 2010

Related U.S. Application Data

(60) Provisional application No. 61/101,671, filed on Sep. 30, 2008.

(51) Int. Cl.
*A61B 5/1455* (2006.01)
*A61M 16/00* (2006.01)

(52) U.S. Cl.
USPC ...................... 600/323; 128/204.23

(58) Field of Classification Search
USPC ............... 600/310, 322, 323; 128/204.23
See application file for complete search history.

(56) References Cited

U.S. PATENT DOCUMENTS

| 6,016,444 | A  | * | 1/2000  | John ............................ 600/544 |
| 6,526,297 | B1 | * | 2/2003  | Merilainen ................... 600/310 |
| 6,615,065 | B1 |   | 9/2003  | Barrett et al. |
| 6,934,579 | B2 | * | 8/2005  | Mantzaridis et al. ......... 600/544 |
| 8,038,645 | B2 | * | 10/2011 | Edginton et al. ............... 604/66 |
| 8,055,321 | B2 | * | 11/2011 | Bernreuter .................... 600/323 |
| 2008/0015424 | A1 |   | 1/2008 | Bernreuter |

FOREIGN PATENT DOCUMENTS

| WO | WO 2006/071891 A2 | 7/2006 |
| WO | WO 2007/079316 A2 | 7/2007 |

OTHER PUBLICATIONS

De Blasi et al., "Effects of remifentanil-based general anaesthesia with propfol or sevoflurane on muscle microcirculation as assessed by near-infrared spectroscopy," British Journal of Anaesthesia, vol. 101 (2), pp. 171-177, Jun. 3, 2008.*

* cited by examiner

*Primary Examiner* — Eric Winakur
(74) *Attorney, Agent, or Firm* — Baker & Hostetler LLP

(57) ABSTRACT

Disclosed are methods and devices for measuring a state of anesthesia in a noninvasive manner. Optical techniques may be used to measure changes in a functional near-infrared (fNIR) signal, where the fNIR signal is received in response to directing wavelengths of light in a near-infrared range on a patient. The optical density change may be used to obtain a change in deoxyhemoglobin (deoxy-Hb) concentration and/or a change in an oxyhemoglobin concentration (oxy-Hb). The changes in the deoxy-Hb and/or the oxy-Hb may then be compared to determine a state of anesthesia.

The effect of artifacts (e.g., strong surgery room lighting, patient-table tilting, patient intubation/extubation) on the fNIR signal may be removed using a noise removal algorithm. In selecting the noise removal algorithm, a switching technique may be used to select the component analysis algorithm, such as a principal component analysis (PCA), an independent component analysis (ICA), or the like.

48 Claims, 9 Drawing Sheets

FUNCTIONAL NEAR-INFRARED SPECTROSCOPY AS A MONITOR FOR DEPTH OF ANESTHESIA

CROSS-REFERENCE TO RELATED APPLICATION

This application claims priority under 35 U.S.C. §119(e) to U.S. provisional application Ser. No. 61/101,671, filed on Sep. 30, 2008, entitled "Functional Near-Infrared Spectroscopy as a Monitor for Depth of Anesthesia," which is herein incorporated by reference in its entirety.

BACKGROUND

It is known that fear, dread, panic, and excruciating pain may accompany unintended awareness during anesthesia. During this anesthesia state, patients may recall events or conversations that occurred in the operation room. These incidents are not benign. For example, some incidents have resulted in posttraumatic stress disorder. Prevention of unintended awareness during anesthesia may be accomplished by having an alert anesthesia clinician monitor an anesthetized patient's vital signs. However, vital signs may not provide a sufficient warning. For example, vital signs may not provide a sufficient warning in elderly anesthetized patients with comorbid conditions such as hypertension or tachycardia.

There has been interest in developing state of anesthesia devices that can continuously and reliably monitor the anesthesia state during a surgical procedure. Such devices have largely been based on the measurement of electrophysiological signals such as electrocardiographic (ECG) signals, electroencephalographic (EEG) signals, auditory and somatosensory evoked potentials, and craniofacial electromographic (EMG) signals. Unfortunately, electrophysiological parameters provide limited accuracy as those parameters involve measuring electric currents and cannot measure biological parameters such as hemodynamic response.

SUMMARY

Disclosed herein are methods and devices for measuring a state of anesthesia in a noninvasive manner using functional near-infrared (fNIR) spectroscopy. For example, fNIR signals may be obtained and processed to measure deoxygenated hemoglobin (deoxy-Hb) and/or oxygenated hemoglobin (oxy-Hb) content. An active brain consumes oxygen transported to the brain by oxy-Hb in the blood. As the oxy-Hb gives up oxygen, the oxy-Hb transforms into deoxy-Hb. Oxy-Hb and deoxy-Hb have characteristic optical properties in the visible and near-infrared (NIR) light range. Accordingly, fNIR may be used to measure concentrations of deoxy-Hb and/or oxy-Hb as a measure of brain activity and the state of anesthesia. As will be described below, optical techniques derived from the physical principles of light absorption and reflectance may be used to detect changes in a neuromarker, such as changes in the hemodynamic response of the cortex. A neuromarker may provide an index of anesthesia, correlating percentages of deoxy-HB to varying levels of cortical activity.

According to an example embodiment, a device may determine the state of anesthesia. The device may include of a light source for emitting near infrared (NIR) light at varying frequencies and/or wavelengths, and a light detector for receiving the NIR light. The light detector may be adapted for detecting concentrations of oxy-Hb and/or deoxy-Hb. A light source, for example, may be any light emitting source such as a light emitting diode (LED), for example, and the light detector may be any device capable of receiving light, such as a photodetector, for example.

In another example embodiment, the state of anesthesia may be determined by measuring an optical density change of NIR light. Two or more wavelengths of NIR light may be directed on a patient and an fNIR signal may be received. The received fNIR signal may be used to measure an optical density change of the NIR light. Using the optical density change, a deoxy-Hb concentration and/or an oxy-Hb concentration and/or a total hemoglobin volume may be obtained. A percentage and/or rate of change of the deoxy-Hb concentration may then be used to determine a state of anesthesia. An amount of an anesthetic may then be administered to either maintain or alter the state of anesthesia. An anesthetic may be any chemical or drug that brings about a state of anesthesia. In another example embodiment, the state of anesthesia may be determined by removing the effect of an artifact from the fNIR signal. An fNIR signal may be emitted and received. A non-cortical signal that may be indicative of an artifact may be included within the received fNIR signal and may be captured. Artifacts within the received fNIR signal may have been caused by strong surgery room lighting, patient-table tilting, patient intubation and extubation, or the like. These artifacts may have an effect on the fNIR signals and may be identified and/or removed by capturing the non-cortical signal indicative of the artifact and removing the non-cortical signal from the fNIR using a noise removal algorithm. In selecting the noise removal algorithm, a switching technique may be used to select the component analysis algorithm such as a principal component analysis (PCA), an independent component analysis (ICA), or the like. The selected noise removal algorithm may then subtract a portion of the non-cortical signal from the fNIR signal. The fNIR signal may be used to measure an optical density change of the NIR light that may then be used to determine the state of anesthesia. An amount of an anesthetic may then be administered to either maintain or alter the state of anesthesia.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION OF ILLUSTRATIVE EMBODIMENTS

Disclosed herein are techniques that may be used for quantitatively evaluating the depth of anesthesia in a noninvasive manner. For example, fNIR signals may be obtained and processed to measure deoxygenated hemoglobin (deoxy-Hb) and/or oxygenated hemoglobin (oxy-Hb) content. An active brain consumes oxygen transported to the brain by oxy-Hb in the blood. As the oxy-Hb gives up oxygen, the oxy-Hb transforms into deoxy-Hb. Oxy-Hb and deoxy-Hb have characteristic optical properties in the visible and near-infrared light range. Accordingly, fNIR may be used to measure concentrations of deoxy-Hb and/or oxy-Hb to measure of brain activity and the state of anesthesia.

Figure 1:
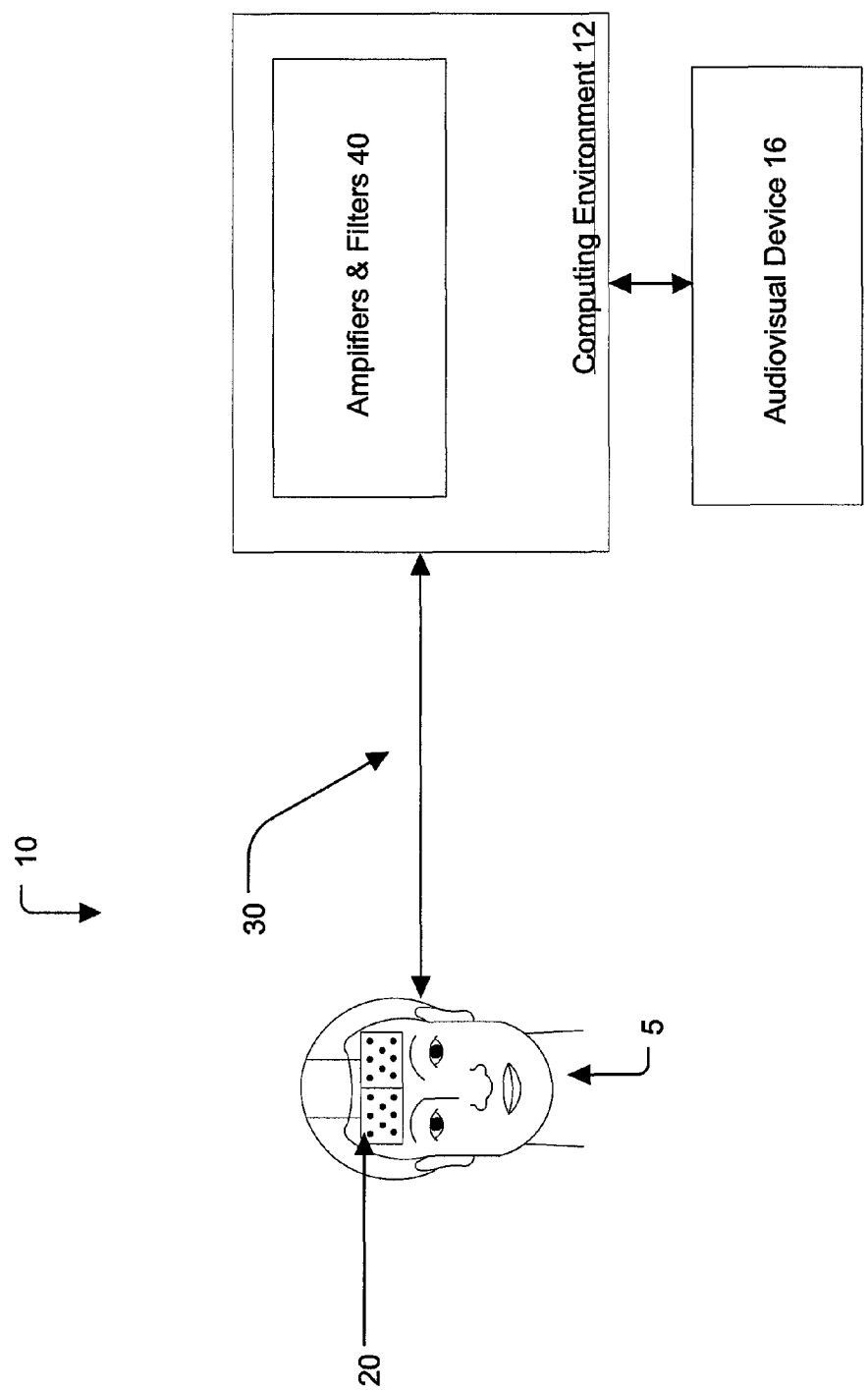
FIG. 1 illustrates an example embodiment of a system that may be used to determine a state of anesthesia.

FIG. 1 illustrates an example embodiment of a system that may be used to determine a state of anesthesia. In an example embodiment, the system 10 may be used to determine and/or track a state of anesthesia of a patient, such as the patient 5.

As shown in FIG. 1 the system 10 may include a computing environment 12. The computing environment 12 may be a computing device such as a computer, a personal digital assistant (PDA), a smartphone or the like. According to an example embodiment, the computing environment 12 may include hardware components and/or software components such that the computing environment 12 may be used to execute applications such an operating system, state of anesthesia monitoring software, or the like. In one embodiment, the computing environment 12 may include a processor, such as a standardized processor, a specialized processor, a microprocessor, or the like, that may execute instructions including, for example, instructions for emitting an fNIR signal, receiving an fNIR signal, determining a state of anesthesia, or any other suitable instruction, which will be described in more detail below. In an example embodiment, the computing environment 12 may contain filters and amplifiers that may be used to power and control a capture device, such as the capture device 20. The filters and amplifiers may be implemented in software, digital hardware, analog hardware, or a combination of software and hardware.

The system 10 may further include a capture device 20. The capture device 20 may be, for example, a device that may direct light at varying wavelengths and receive an fNIR signal after it has passed through human tissue, such as the tissue of patient 5, as will be described in more detail below. In another embodiment, which will also be described in more detail below, the capture device 20 may further be used to determine a state of anesthesia for a patient, such as patient 5. The capture device 20 may connected to the computing environment 12 via, for example, via a coaxial cable, an Ethernet cable, an HDMI cable, a DVI cable, a VGA cable, or the like. In another example embodiment, the capture device 20 may also be connected to the computing environment 12 via a wireless network such as Bluetooth, Wi-Fi, IEEE 802.11, ZigBee, or the like.

According to one embodiment, system 10 may be connected to an audiovisual device 16 such as a television, a monitor, a high-definition television (HDTV), or the like that may provide visuals and/or audio for the monitoring state of anesthesia. For example, the computing environment 12 may include a video adapter, such as a graphics card, and/or an audio adapter, such as a sound card, that may provide audiovisual signals associated with the game application, non-game application, or the like. The audiovisual device 16 may receive the audiovisual signals from the computing environment 12 and may output the game or application visuals and/or audio associated with the audiovisual signals to the user 18. According to one embodiment, the audiovisual device 16 may be connected to the computing environment 12 via, for example, an S-Video cable, a coaxial cable, an HDMI cable, a DVI cable, a VGA cable, or the like.

Figure 2:
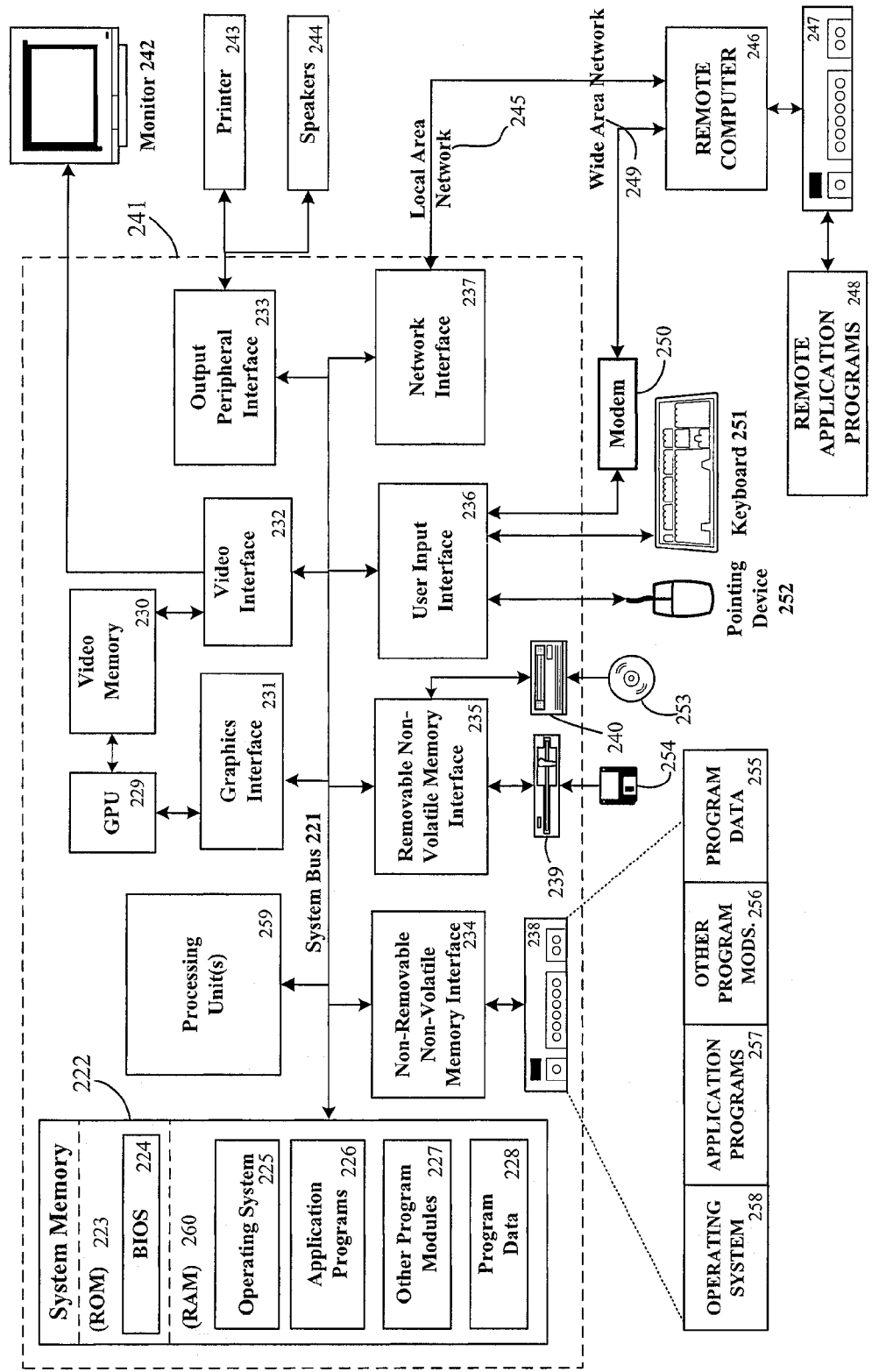
FIG. 2 illustrates an example embodiment of a computing environment that may be used to determine a state of anesthesia.

FIG. 2 illustrates an example embodiment of a computing environment 220 that may be the computing environment 12 shown with respect to FIG. 1 used to determine a state of anesthesia. The computing system environment 220 is only one example of a suitable computing environment and is not intended to suggest any limitation as to the scope of use or functionality of the presently disclosed subject matter. Neither should the computing environment 12 be interpreted as having any dependency or requirement relating to any one or combination of components illustrated in the exemplary operating environment 220. In some embodiments, the various depicted computing elements may include circuitry configured to instantiate specific aspects of the present disclosure. For example, the term circuitry used in the disclosure may include specialized hardware components configured to perform function(s) by firmware or switches. In other examples embodiments the term circuitry may include a general-purpose processing unit, memory, etc., configured by software instructions that embody logic operable to perform function(s). In example embodiments where circuitry includes a combination of hardware and software, an implementer may write source code embodying logic and the source code may be compiled into machine-readable code that may be processed by the general-purpose processing unit. Since one skilled in the art may appreciate that the state of the art has evolved to a point where there is little difference between hardware, software, or a combination of hardware/software, the selection of hardware versus software to effectuate specific functions is a design choice left to an implementer. More specifically, one of skill in the art may appreciate that a software process may be transformed into an equivalent hardware structure, and a hardware structure may itself be transformed into an equivalent software process. Thus, the selection of a hardware implementation versus a software implementation is one of design choice and left to the implementer.

In FIG. 2, the computing environment 220 comprises a computer 241, which typically includes a variety of computer readable media. Computer readable media may be any available media that may be accessed by computer 241. Computer readable media includes both volatile and nonvolatile media, removable and non-removable media. The system memory 222 includes computer storage media in the form of volatile and/or nonvolatile memory such as read only memory (ROM) 223 and random access memory (RAM) 260. A basic input/output system 224 (BIOS), including the basic routines that help to transfer information between elements within computer 241, such as during start-up, is typically stored in ROM 223. RAM 260 typically includes data and/or program modules that are immediately accessible to and/or presently being operated on by processing unit 259. By way of example, and not limitation, FIG. 2 illustrates operating system 225, application programs 226, other program modules 227, and program data 228.

The computer 241 may also include other removable/non-removable, volatile/nonvolatile computer storage media. By way of example only, FIG. 2 illustrates a hard disk drive 238 that reads from or writes to non-removable, nonvolatile magnetic media, a magnetic disk drive 239 that reads from or writes to a removable, nonvolatile magnetic disk 254, and an optical disk drive 240 that reads from or writes to a removable, nonvolatile optical disk 253 such as a CD ROM or other optical media. Other removable/non-removable, volatile/nonvolatile computer storage media that may be used in the exemplary operating environment include, but are not limited to, magnetic tape cassettes, flash memory cards, digital versatile disks, digital video tape, solid state RAM, solid state ROM, and the like. The hard disk drive 238 is typically connected to the system bus 221 through an non-removable memory interface such as interface 234, and magnetic disk drive 239 and optical disk drive 240 are typically connected to the system bus 221 by a removable memory interface, such as interface 235.

The drives and their associated computer storage media discussed above and illustrated in FIG. 2, provide storage of computer readable instructions, data structures, program modules and other data for the computer 241. In FIG. 2, for example, hard disk drive 238 is illustrated as storing operating system 258, application programs 226, other program modules 227, and program data 228. Note that these components may either be the same as or different from operating system 225, application programs 226, other program modules 227, and program data 228. Operating system 225, application programs 226, other program modules 227, and program data 228 are given different numbers here to illustrate that at, a minimum, they are different copies. A user may enter commands and information into the computer 241 through input devices such as a keyboard 251 and pointing device 252, commonly referred to as a mouse, trackball or touch pad. Other input devices (not shown) may include a microphone, joystick, game pad, satellite dish, scanner, or the like. These and other input devices are often connected to the processing unit 259 through a user input interface 236 that is coupled to the system bus, but may be connected by other interface and bus structures, such as a parallel port, game port or a universal serial bus (USB). The capture device 20, as shown in FIGS. 1-3B, may define an additional input device. A monitor 242 or other type of display device is also connected to the system bus 221 via an interface, such as a video interface 232. In addition to the monitor, computers may also include other peripheral output devices such as speakers 244 and printer 243, which may be connected through a output peripheral interface 233.

The computer 241 may operate in a networked environment using logical connections to one or more remote computers, such as a remote computer 246. The remote computer 246 may be a personal computer, a server, a router, a network PC, a peer device or other common network node, and typically includes many or all of the elements described above relative to the computer 241, although only a memory storage device 247 has been illustrated in FIG. 2. The logical connections depicted in FIG. 2 include a local area network (LAN) 245 and a wide area network (WAN) 249, but may also include other networks. Such networking environments are commonplace in offices, enterprise-wide computer networks, intranets and the Internet.

When used in a LAN networking environment, the computer 241 is connected to the LAN 245 through a network interface or adapter 237. When used in a WAN networking environment, the computer 241 typically includes a modem 250 or other means for establishing communications over the WAN 249, such as the Internet. The modem 250, which may be internal or external, may be connected to the system bus 221 via the user input interface 236, or other appropriate mechanism. In a networked environment, program modules depicted relative to the computer 241, or portions thereof, may be stored in the remote memory storage device. By way of example, and not limitation, FIG. 2 illustrates remote application programs 248 as residing on memory device 247. It will be appreciated that the network connections shown are exemplary and other means of establishing a communications link between the computers may be used.

Figure 3B:
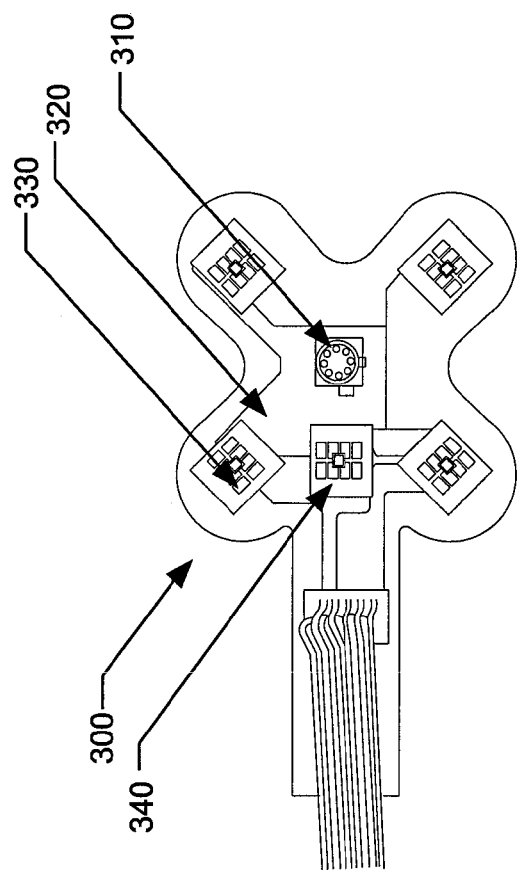
FIGS. 3A, 3B illustrate example embodiments of devices for determining a state of anesthesia.
Figure 3A:
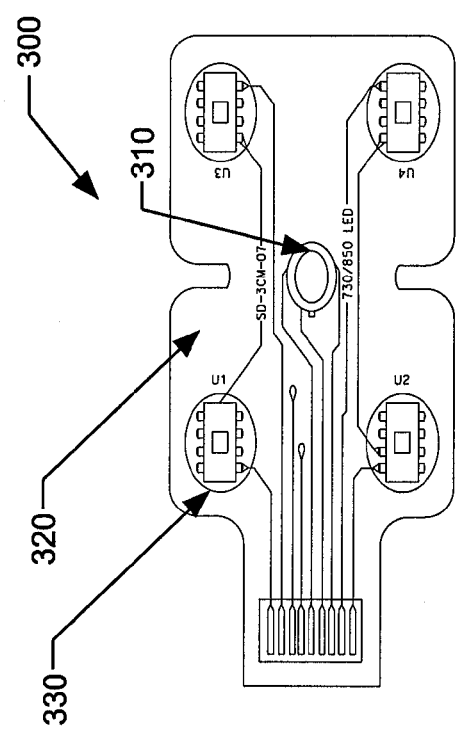

FIG. 3A illustrates an example embodiment of a device 300 for determining a state of anesthesia. The example device may be the capture device 20 with respect to FIG. 1-3B. The capture device may be used, for example, with the computing device 12 of the system 10, described with respect to FIG. 1, to determine a state of anesthesia of a patient, such as the patient 5.

In one example embodiment, the device 300 may contain a light source, such as the light source 310. The light source 310 may be a light emitting diode, an incandescent light bulb, a cathode ray tube, or the like. The light source may emit NIR light at varying wavelengths. For example, the light source may emit NIR the light that may mostly absorbed by oxy-Hb and/or deoxy-Hb.

Figure 4:
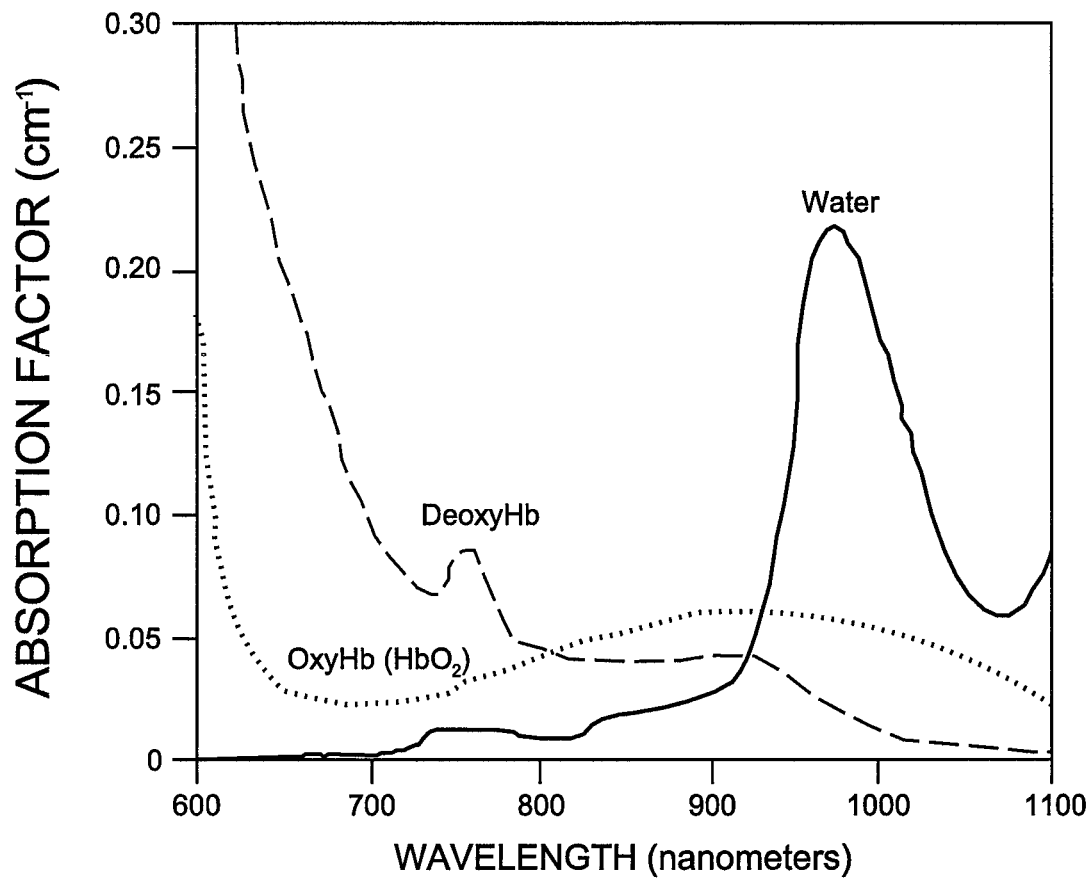
FIG. 4 illustrates a range of wavelengths that may be used to determine a state of anesthesia.

As shown in FIG. 4, in one embodiment, the light source may emit light in the NIR range between 700-900 nm. In this range, water, a major component of most tissues, may absorb very little energy while the spectra of oxy-Hb and deoxy-Hb may be distinct enough to allow spectroscopy and measures of separate concentrations of both oxy-Hb and deoxy-Hb molecules.

Returning to FIG. 3A, in another embodiment, the light source may emit two or more wavelengths of the NIR light in a range between 700 nm and 900 nm. For example, the light source may emit a first wavelength of 730 nm and a second wavelength of 850 nm. The two or more wavelengths of the NIR light may be absorbed by the deoxy-Hb or the oxy-Hb.

Figure 5:
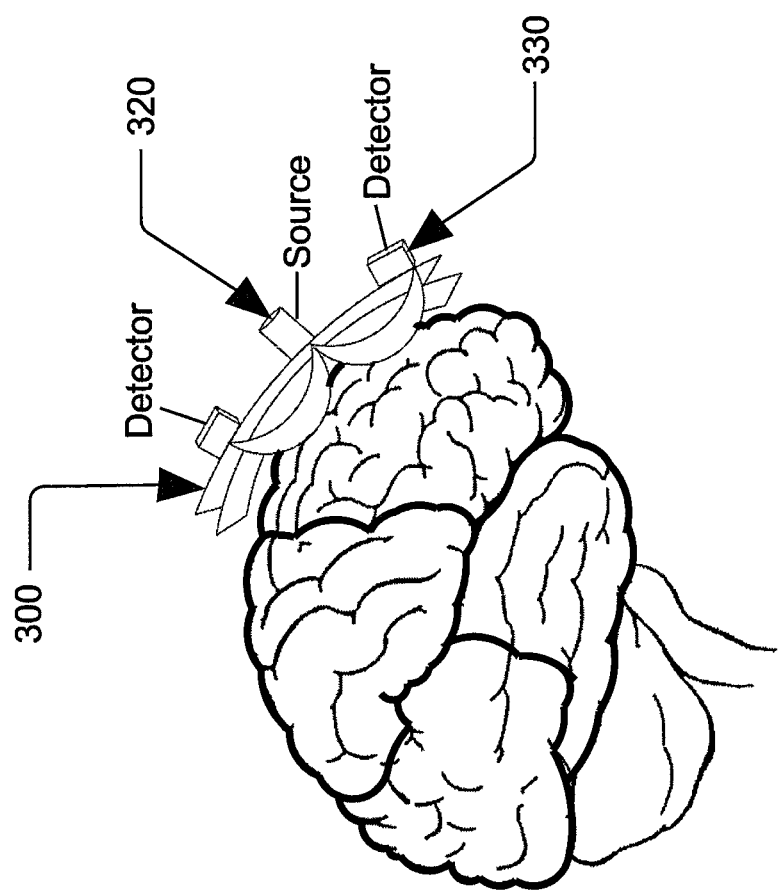
FIG. 5 illustrates an example embodiment of a device for determining a state of anesthesia.

As shown in FIG. 5, the light source 310 may emit NIR light at or near a patient's scalp and may pass through layers of tissue. For example, the light source may be directed at a prefrontal cortex of a patient. The NIR light may be absorbed and scattered by the oxy-Hb and deoxy-Hb. A predictable quantity of photons may follow a 'banana-shaped' path and leave the tissue and may be measured using photodetectors, such as the light detector 330, as will be described below.

Returning to FIG. 3A, in another embodiment, the light source may emit two or more wavelengths of the NIR light in a range between 700 nm and 900 nm. For example, the light source may emit a first wavelength of 730 nm and a second wavelength of 850 nm. The two or more wavelengths of the NIR light may be absorbed by the deoxy-Hb or the oxy-Hb.

In another example embodiment, the device 300 may contain a light detector, such as the light detector 330. The light detector 330 may be a photodetector, a sensor, or the like. The light detector may capture and/or receive an fNIR signal in response to directing the wavelengths of NIR light on the patient, emitted by the light source 310. For example, the light detector may receive the fNIR signal after the fNIR signal has passed through human tissue. To assist the light detector 330 in receiving NIR light, the light detector may be placed a distance, such as 2.5 cm or 3 cm, away from the light source. This distance may enable the light detector 320 to receive NIR light that may travel along a banana shaped path between the light source 320 and the light detector 330. The light detector 330 may be used to measure a portion of the NIR light that may not absorbed by human tissue. In another example embodiment, the light detector 330 may be adapted to detect a relative change in the percentage of deoxy-Hb in a total blood volume, as will be further described below.

In another example embodiment, the light detector 330 may receive NIR light that may contain non-cortical signals and/or artifacts may be received. The received NIR light may contain various wavelengths of fNIR signals that were emitted by a device, such as the device 300. For example, the light detector may receive NIR light that has passed through human tissue. The received NIR light may contain a non-cortical signal that may indicative of an artifact. Artifacts within the received NIR light may have been caused by strong surgery room lighting, patient-table tilting, patient intubation and extubation, or the like. These artifacts may affect the NIR light.

The device 300 may include a flexible circuit, such as the flexible circuit 320. The flexible circuit 320 may be a disposable single-use cushioning material that may attach to the patient's forehead. The flexible circuit 320 may provide a reliable integrated wiring solution and consistent component spacing. The flexible circuit 320 may enable the device 300 to adapt to the various contours of the patient's head. For example, the flexible circuit 320 may allow the device 300 to be placed in such a way that the light detectors are able to maintain an orthogonal orientation to the skin surface. This orientation may dramatically improving light coupling efficiency and signal strength.

FIG. 3B illustrates an additional example embodiment a device 300 for determining a state of anesthesia. The device 300 may include a light detector, such as the light detector 340, that may be used to capture a reference signal. This reference signal may be used to remove noise from the fNIR signals that may be used to measure oxy-Hb and/or deoxy-Hb. For example, the reference signal may be emitted to capture non-cortical signals during a period of minimal activation. These non-cortical signals may be used to calibrate and/or remove noise from the other received fNIR signals light. In one example embodiment, the light detector 340 may be placed at a distance from the light source 310 that differs from the distance between light detector 330 and the light source 310.

In another example embodiment, the light detector 340 may receive NIR light that may contain non-cortical signals and/or artifacts may be received. The received NIR light may contain various wavelengths of NIR light emitted by a device such as the device 300. For example, the light detector 340 may receive NIR light that has passed through human tissue. The received NIR light may contain a non-cortical signal that may be indicative of an artifact. Artifacts within the received fNIR signal may have been caused by strong surgery room lighting, patient-table tilting, patient intubation and extubation, or the like. These artifacts may affect the NIR light.

Figure 6:
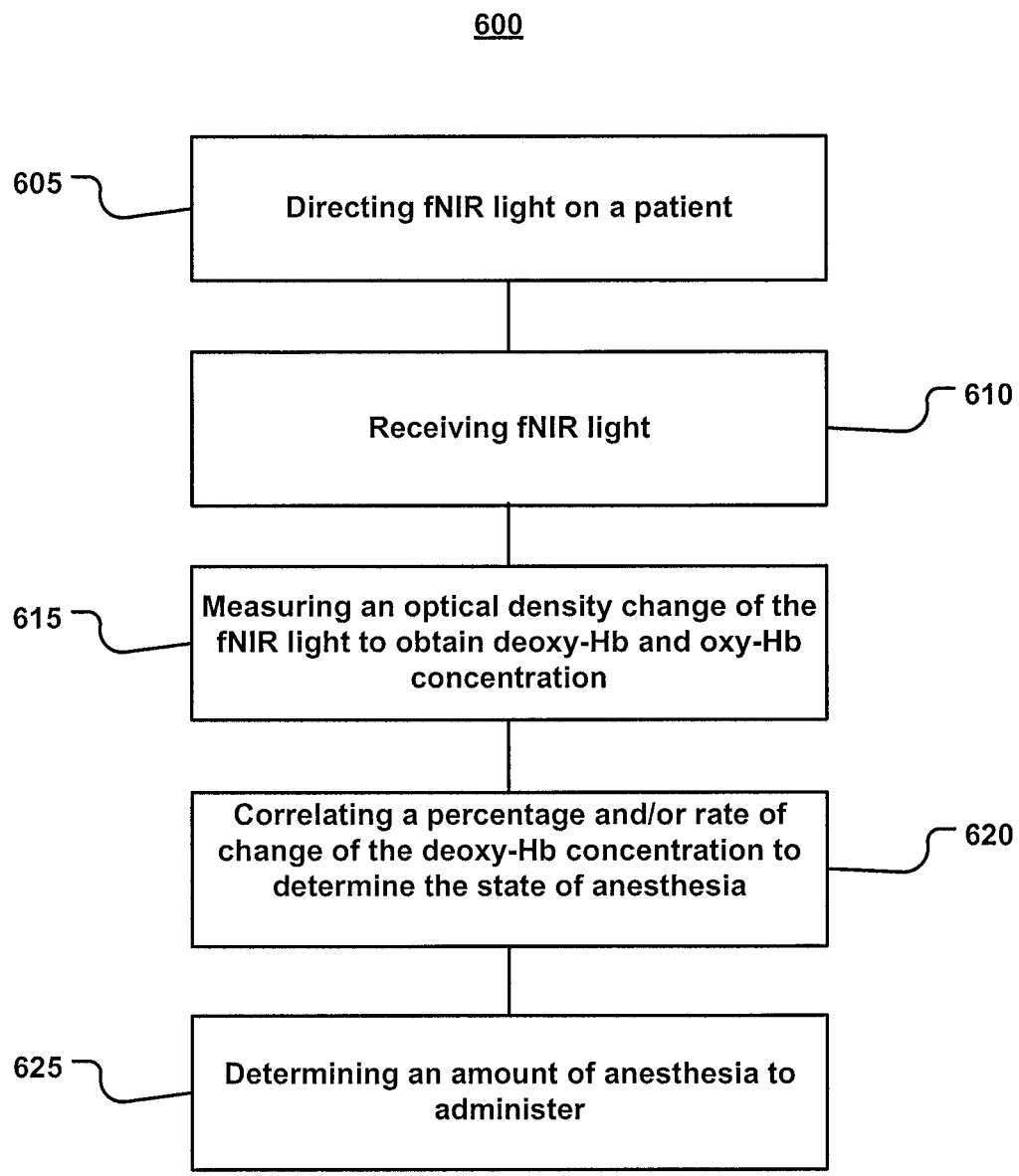
FIG. 6 depicts a flow diagram of an example method for determining a state of anesthesia by measuring an optical density change of NIR light.

FIG. 6 depicts a flow diagram of an example method for determining a state of anesthesia by measuring an optical density change of NIR light. The example method may be implemented using, for example, the device 20 and/or the computing device 220 of the system 10 described with respect to FIGS. 1-3. In an example embodiment, the method may take the form of program code (i.e., instructions) that may be executed by, for example, the capture device 20 and/or the computing environment 12 of the system 10 described with respect to FIG. 1-3.

According to an example embodiment, at 605, NIR light may be directed on a patient, such as the patient 5 shown with respect to FIG. 1. The NIR light may be directed by a light emitting diode, an incandescent light bulb, a cathode ray tube, or the like. The directed NIR light may be at varying wavelengths and may have the same characteristic optical properties as oxy-Hb and deoxy-Hb.

In one example embodiment, two or more wavelengths of NIR light in a range between 700 nm and 900 nm may be directed on a patient. For example, the light source may emit a first wavelength of 730 nm and a second wavelength of 850 nm. The two or more wavelengths of the NIR light may be absorbed by the deoxy-Hb or the oxy-Hb.

In another example embodiment, the NIR light may be directed at a frontal cortex of the patient. For example, the fNIR may be directed at or near a patient's scalp. The fNIR may pass through layers of tissue and may be absorbed and scattered by the oxy-Hb and deoxy-Hb. As shown in FIG. 5, a predictable quantity of NIR light may follow a 'banana-shaped' path and leave the tissue.

Referring back to FIG. 6, at 610, NIR light may be received. The NIR light may be captured and/or received at varying frequencies and/or wavelengths. For example, NIR light at a wavelength of 730 nm may be received. In one embodiment, the device 300 may have emitted the received NIR light. In another embodiment, the received NIR light may have passed through human tissue.

At 615, an optical density change of the fNIR signal may be measured to obtain a deoxy-Hb concentration and/or relative to an oxy-Hb concentration. In one embodiment, the optical density change may be measured by determining the amount of NIR light that undergoes absorption and scattering by tissue. For example, under the modified Beer-Lambert Law the optical density after absorption and scattering of the biological tissue may be measured by using the equation:

$$I = GI_o e^{-(\alpha_{HB} C_{HB} + \alpha_{HBO2} C_{HBO2})*L}$$

In the above equation G may be a factor that accounts for the measurement geometry and may be assumed constant when concentration changes. $I_o$ is input light intensity, $\alpha_{HB}$ and $\alpha_{HBO2}$ are the molar extinction coefficients of deoxy-Hb and oxy-Hb, $C_{HB}$ and $C_{HBO2}$ are the concentrations of deoxy-Hb and oxy-Hb respectively, and L is the photon path which is a function of absorption and scattering coefficients $\mu_a$ and $\mu_b$. By measuring optical density changes at two wavelengths, the relative change of deoxy-Hb and oxy-Hb versus time may be obtained. For example, if the intensity measurement at an initial time is $I_b$ (baseline), and at another time is I, the optical density change due to variation in concentrations of deoxy-Hb and oxy-Hb during that period is:

$$\Delta OD = \log_{10} \frac{I_b}{I} = \alpha_{HB} \Delta C_{HB} + \alpha_{HBO_2} \Delta C_{HBO_2}$$

In an another example embodiment, measuring the optical density change of the NIR light may comprise measuring an absorption of each of the two or more wavelengths of the NIR light after directing the fNIR on the patient. For example, absorbance and/or scattering changes at two or more wavelengths may be measured. One of the wavelengths used may be more sensitive to oxy-Hb than to deoxy-Hb. Changes in the relative concentration of these oxy-Hb and deoxy-Hb may then be calculated using the two or more wavelengths.

In another example embodiment, a baseline deoxy-Hb may be calculated by measuring the optical density change of the fNIR. In calculating the baseline deoxy-Hb, the fNIR signal may be obtained prior to administering anesthesia. For example, the baseline fNIR may be determined 20 seconds before administering anesthesia. This may be performed to provide an understanding of the deoxy-Hb and/or oxy-Hb levels on a patient-by-patient basis before anesthesia may be administered. The baseline fNIR may represent the deoxy-Hb concentration levels, or may be a ratio, such as a ratio of deoxy-Hb to oxy-Hb, or the like.

In another example embodiment, a percentage of deoxy-Hb concentration may be a ratio of the deoxy-Hb to at least one of an oxy-Hb concentration, a baseline deoxy-Hb, or a total hemoglobin volume. Measurements may be performed at two or more different wavelengths and may allow for the calculation of changes in concentrations of deoxy-Hb ($\Delta C_{HB}$) and oxy-Hb ($\Delta C_{HBO2}$). Change in oxygenation and blood volume or total hemoglobin (Hbt) may then be deduced using the following equation:

$$\text{Oxygenation} = \Delta C_{HBO_2} - \Delta C_{HB}$$

The percentage of deoxy-Hb concentration may then be calculated as a ratio of the deoxy-Hb to at least one of an oxy-Hb concentration, a baseline deoxy-Hb, or a total hemoglobin volume. In one example embodiment, the percentage and/or ratio of deoxy-Hb may be measured at a sample rate, such as a 2 Hz sample rate, and may be measured in real time.

At 620, a percentage and/or rate of change of the deoxy-Hb concentration may be correlated to determine the state of anesthesia. Anesthetics may have direct cerebral vasodilatory effects and may increase cerebral blood flow. Increases in cerebral blood flow are generally followed by increases in cerebral blood volume. The increases in cerebral blood volume may cause excessive amount of Hbt, oxy-Hb and deoxy-Hb during deep anesthesia and may be caused by a combination of the decrease in neuronal metabolic demand coupled with an increase in cerebral blood floor.

Figure 7:
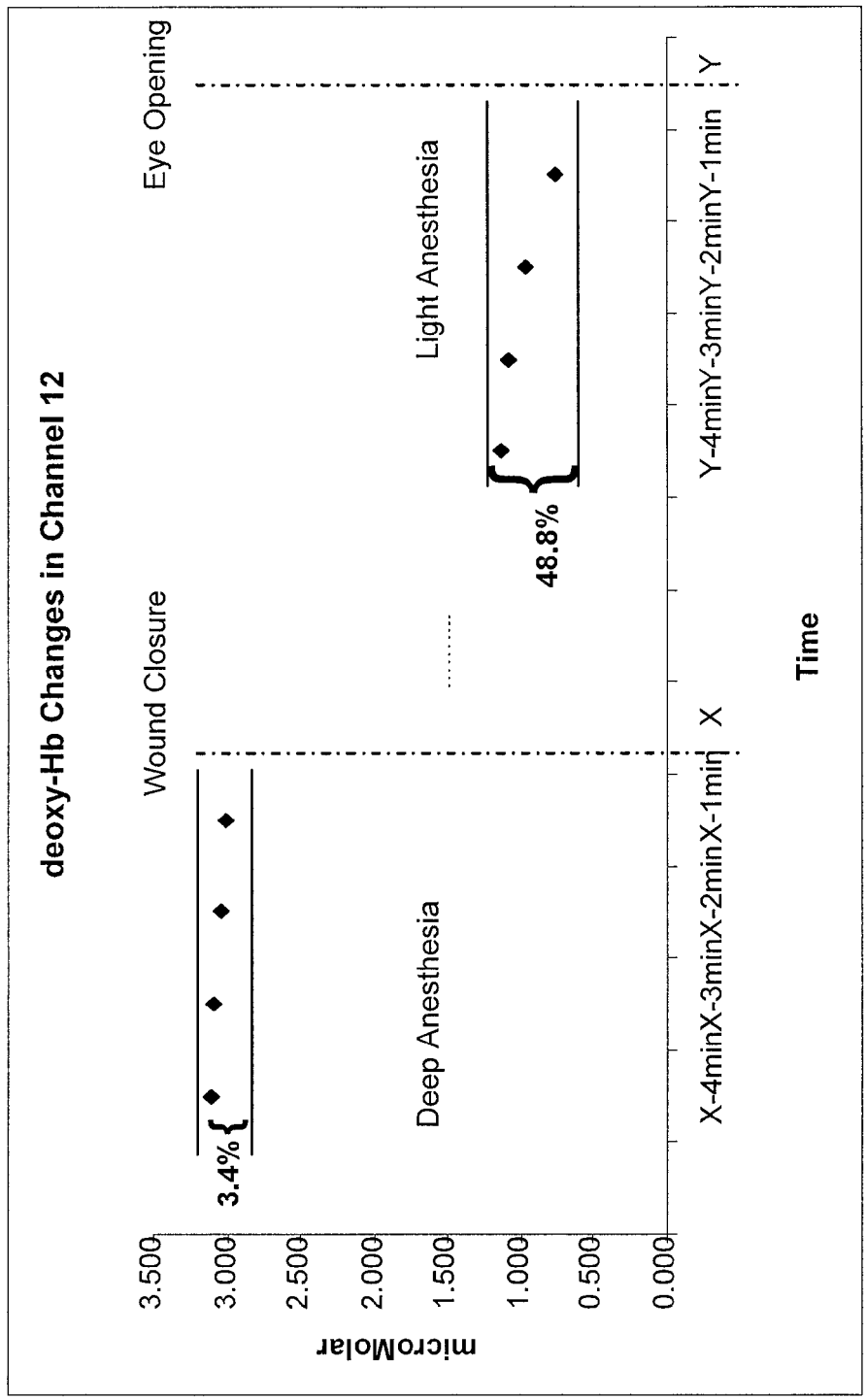
FIG. 7 illustrates deoxygenated hemoglobin concentrations that may indicate a state of anesthesia.

In one example embodiment, the decreases in percentage and/or rate of deoxy-Hb changes during deep anesthesia may be monitored and correlated to the cerebral metabolic rate (demand) suppression by the administered anesthetic agents. For example, as shown in FIG. 7, Deoxy-Hb concentration may indicate a changing state of anesthesia as light anesthesia may be associated with relatively less deoxy-Hb concentration than deep anesthesia. Additionally, a change, such as a decrease, in the percentage of deoxy-Hb may be an indication of changing levels of cortical activity, such as increased cortical activity, and/or an emergence from anesthesia. For example, deoxy-Hb averages may demonstrate a very slow rate of change in deep anesthesia, whereas this rate of change may be drastically increased when the patient emerges to wakefulness. A neuromarker may provide an index of anesthesia that correlates levels of cortical activity to the varying states of anesthesia. For example, the neuromarker may indicate a percentage of deoxy-HB or a percentage range of deoxy-HB to a level of cortical activity that correlates to a deep state of anesthesia. Returning to FIG. 6, in one embodiment, cortical activity may correspond to at least one of a state of anesthesia, a transition between states of anesthesia, or a risk level that corresponds to an emergence from anesthesia. The neuromarker may indicate the state of anesthesia or a changing state of anesthesia by identifying the rate of change in cortical activity. For example, a slow rate of change in the percentage of deoxy-HB may be an indication of a deep state of anesthesia. The neuromarker may be extracted from fNIR measurements particular to a single patient or based on a collection of data from multiple patients.

In another example embodiment, the state of anesthesia may be determined by comparing the percentage of deoxy-Hb to the baseline deoxy-Hb. The baseline deoxy-Hb may indicate the deoxy-Hb concentration and/or ratio that may exist in a patient prior to the administration of anesthesia and may indicate the deoxy-Hb levels that correlate to a state of awareness. After anesthesia is administered, a deoxy-Hb percentage and/or rate may be calculated. The deoxy-Hb percentage and/or rate may then be compared to the baseline deoxy-Hb to determine the state of anesthesia. For example, a deoxy-Hb concentration that is higher than the baseline deoxy-Hb concentration may indicate that the state of anesthesia is deep or light anesthesia.

In one example embodiment, a state of anesthesia may be described in terms of intraoperative data such as times of anesthetic induction, first surgical incision, and wound closure as well as administration of medication. In another example embodiment, a state of anesthesia may be described in terms of the amount of brain activity desired during a phased of a procedure. For example, the state of anesthesia may be a deep state of anesthesia defined as the four-minute time interval prior to wound closure, or a light state of anesthesia defined as the four-minute time interval prior to eye opening. The state of anesthesia may also be an emergence state of anesthesia defined as any time interval where the anesthetic agents may not prevent patient awareness.

At 625, an amount of an anesthetic to administer may be determined. In one embodiment, the amount of anesthesia may be determined according to the state of anesthesia. For example, if the state of anesthesia indicates patient awareness, an amount of an anesthetic may be administered to prevent awareness. In another example embodiment, the levels of deoxy-Hb may be used to administer the minimal dose of anesthetic required to achieve the desired depth of anesthesia. For example, by monitoring the levels of deoxy-Hb, the effectiveness of anesthesia on a patient may be determined. Upon determining the effectiveness of anesthesia, a dosage of anesthesia may be provided to alter the levels of deoxy-Hb and to achieve the desired depth of anesthesia. The administration of anesthesia may include intravenous drug doses, such as Fentanyl, Propofol, or the like, and inhalational drugs, such as Sevoflurane, Desflurane, or the like.

Figure 8:
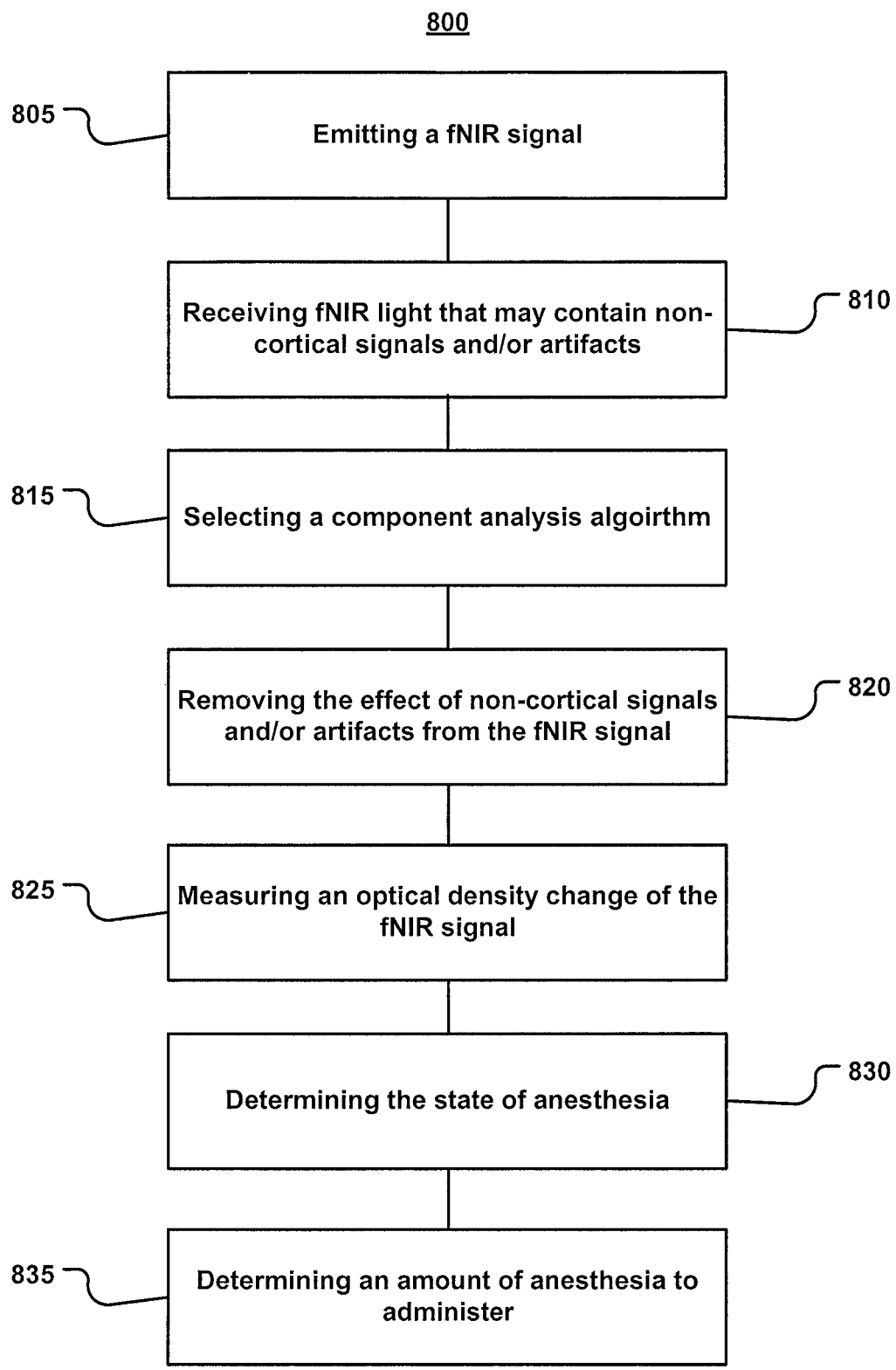
FIG. 8 depicts a flow diagram of an example method for determining a state of anesthesia by removing the effect of an artifact from an fNIR signal.

FIG. 8 depicts a flow diagram of an example method for determining a state of anesthesia by removing the effect of an artifact from the fNIR signal. The example method may be implemented using, for example, the device 20 and/or the computing device 220 of the system 10 described with respect to FIGS. 1-3. In an example embodiment, the method may take the form of program code (i.e., instructions) that may be executed by, for example, the capture device 20 and/or the computing environment 12 of the system 10 described with respect to FIG. 1-3.

According to an example embodiment, at 805, fNIR signals may be emitted. The fNIR signals may be emitted by a light emitting diode, an incandescent light bulb, a cathode ray tube, or the like. The fNIR signals emitted may comprise varying frequencies and/or wavelengths and may have the same characteristic optical properties as oxy-Hb and deoxy-Hb.

In one example embodiment, two or more wavelengths of fNIR signals in a range between 700 nm and 900 nm may be emitted. For example, a first wavelength of 730 nm and a second wavelength of 850 nm may be emitted. The two or more wavelengths of the fNIR signals may be absorbed by the deoxy-Hb or the oxy-Hb.

In another example embodiment, the fNIR signal may include at least three wavelengths. In one embodiment, at least one wavelength may be not emitted, for example utilized at dark-current condition, to capture a reference signal. This reference signal may be used to remove noise from the fNIR signals that may be used to measure oxy-Hb and/or deoxy-Hb. For example, the reference signal may only capture non-cortical signals during a period of no-emitting light condition, which may be known as dark current condition. These non-cortical signals may then be used to calibrate and/or remove noise from the other emitted signals.

In another example embodiment, the fNIR signal may be emitted at a frontal cortex of the patient. For example, the fNIR signal may be emitted at or near a patient's scalp. The fNIR signal may pass through layers of tissue and may be absorbed and scattered by the oxy-Hb and deoxy-Hb. As shown in FIG. 5, a predictable quantity of fNIR signal may follow a banana-shaped path and leave the tissue.

Referring back to FIG. 8, at 810, an fNIR signal that may contain non-cortical signals and/or artifacts may be received. The received fNIR signal may contain various wavelengths of fNIR signals emitted by a device, such as the device 300. For example, the fNIR signal may be received after the fNIR signal has passed through human tissue. The received fNIR signal may also contain a non-cortical signal that may be indicative of an artifact. Artifacts within the received fNIR signal may have been caused by strong surgery room lighting, patient-table tilting, patient intubation and extubation, or the like. These artifacts may have an effect on the fNIR signal.

At 815, a switching technique may be used to select the component analysis algorithm such as a principal component analysis (PCA), an independent component analysis (ICA), or the like. Artifacts signals may be identified and/or removed by capturing the non-cortical signal indicative of the artifact and removing the non-cortical signal from the fNIR using a component analysis algorithm. In selecting the component analysis algorithm, a switching technique may be used to select the component analysis algorithm that performs better.

Figure 9:
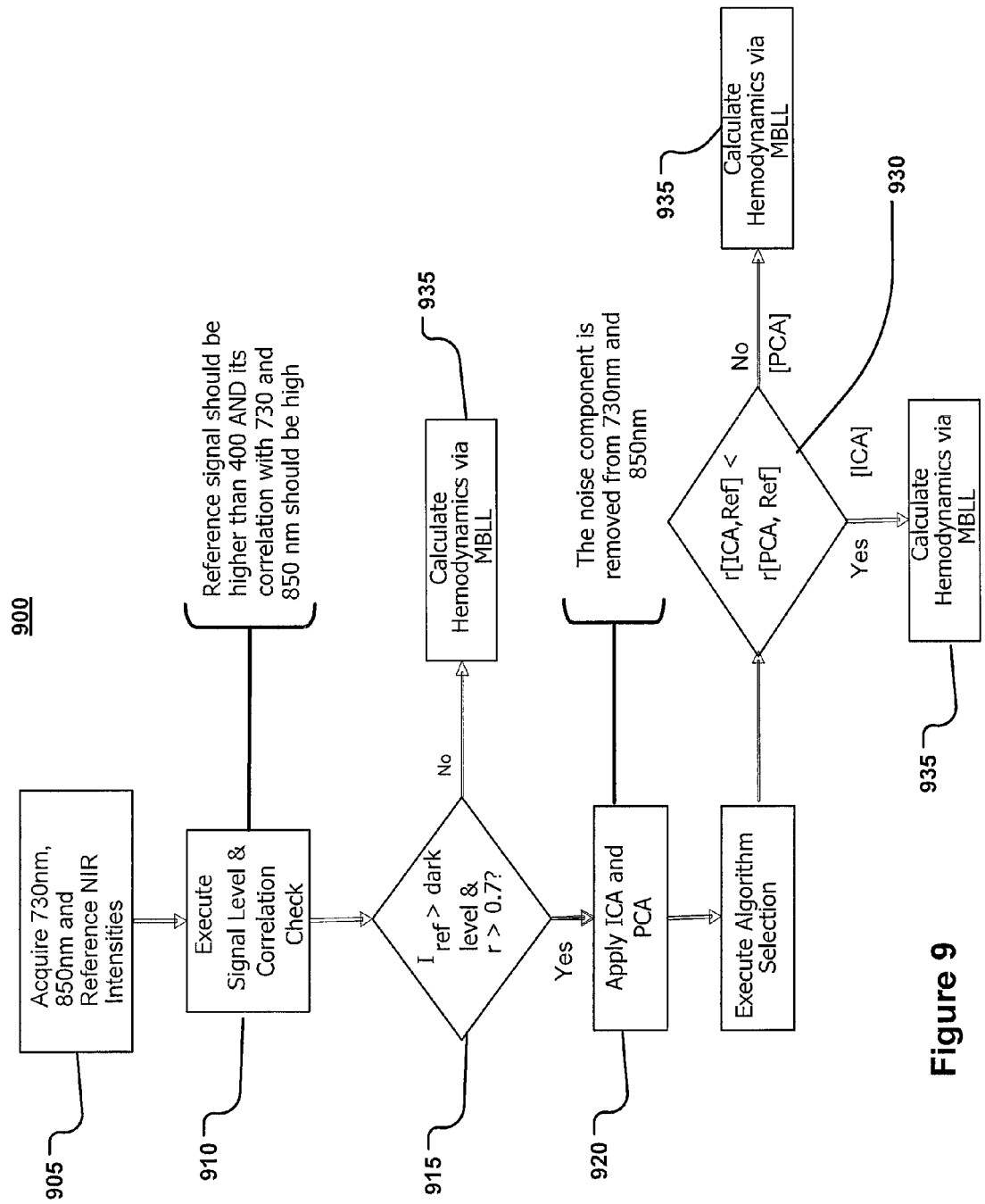
FIG. 9 depicts a flow diagram of an example method for removing the effect of an artifact from an fNIR signal.

For example, FIG. 9 demonstrates that for each wavelength measurement either at 730 nm or 850 nm, a separate ICA and PCA algorithm may be performed where the measurement vector x(t) may be a two dimensional containing the measurement obtained either at 730 or at 850 nm and the one at the reference signal The unknown independent/uncorrelated source signals s(t) that may be estimated by the ICA/PCA algorithm may also be two dimensional which will be the non-physiological noise signal and the clean raw intensity signal related with hemodynamic changes due to cognitive activity. Once the unknown A matrix and the unknown source signals s(t) are extracted, the noise signal may be selected by correlating the independent components with the reference signal separately and selecting the one analysis giving the highest correlation.

In an example embodiment, the reference signal may be received in response to absence of light emitting during a period of dark current condition. The reference signal may be obtained in the environment in which the patient will be anesthetized prior to activity in the environment. For example, the reference signal may be received prior to activity that causes a hemodynamic response, such as patient movement, lighting, extubation, intubation, or the like. The lights may be minimal or off during receipt of the reference signal.

Returning to FIG. 8, at 820, the effect of an artifact may be removed from the fNIR signal. In one embodiment, the selected component analysis algorithm may be used to remove the effect of the artifact from the fNIR signal by subtracting a portion of the non-cortical signal from the fNIR signal.

For example, FIG. 9 demonstrates that after the independent component corresponding to the noise signal has been selected, the noise may be removed from the original 730 nm or 850 nm recordings by subtracting it from that measurement with an appropriate amount, such as the amount the estimated A matrix described above. Correlation between the reference signal measurement and the noise removed intensity measurements via ICA and PCA algorithms are calculated separately. The outcome of the best performing algorithm that generates lowest correlation may be selected as the cleaned raw intensity measurement.

Returning to FIG. 8, at 825, an optical density change of the fNIR signal may be measured to obtain a deoxy-Hb concentration and/or to an oxy-Hb concentration. In one embodiment, the optical density change may be measured by determining the amount of fNIR signal that undergoes absorption and/or scattering by tissue. For example, under the modified Beer-Lambert Law the optical density after absorption and scattering of the biological tissue may be measured by using the equation:

$$I = GI_o e^{-(\alpha_{HB} C_{HB} + \alpha_{HBO2} C_{HBO2})*L}$$

In the above equation G may be a factor that accounts for the measurement geometry and may be assumed constant when concentration changes. $I_o$ is input light intensity, $\alpha_{HB}$ and $\alpha_{HBO2}$ are the molar extinction coefficients of deoxy-Hb and oxy-Hb, $C_{HB}$ and $C_{HBO2}$ are the concentrations of deoxy-Hb and oxy-Hb, respectively and L is the photon path which is a function of absorption and scattering coefficients $\mu_a$ and $\mu_b$. By measuring optical density changes at two wavelengths, the relative change of deoxy-Hb and oxy-Hb versus time may be obtained. For example, if the intensity measurement at an initial time is $I_b$ (baseline), and at another time is I, the optical density change due to variation in concentrations of deoxy-Hb and oxy-Hb during that period is:

$$\Delta OD = \log_{10} \frac{I_b}{I} = \alpha_{HB} \Delta C_{HB} + \alpha_{HBO_2} \Delta C_{HBO_2}$$

In an another example embodiment, measuring the optical density change of the fNIR signal may comprise measuring an absorption of each of the two or more wavelengths of the fNIR signal after directing the fNIR signal on the patient. For example, absorbance and/or scattering changes at two or more wavelengths may be measured. One of the wavelengths used may be more sensitive to oxy-Hb than to deoxy-Hb. Changes in the relative concentration of these oxy-Hb and deoxy-Hb may then be calculated using the two or more wavelengths.

In another example embodiment, a baseline deoxy-Hb may be calculated by measuring the optical density change of the fNIR signal. In calculating the baseline deoxy-Hb, the fNIR signal may be obtained prior to an administration of anesthesia. For example, the baseline fNIR may be determined 20 seconds before the administration of anesthesia. This may be performed to provide an understanding of the deoxy-Hb levels in on a patient-by-patient basis before anesthesia may be administered.

In another example embodiment, a percentage of deoxy-Hb concentration may be a ratio of the deoxy-Hb to at least one of an oxy-Hb concentration, a baseline deoxy-Hb, or a total hemoglobin volume. Measurements may be performed at two or more different wavelengths and may allow for the calculation of allow the calculation of changes in concentrations of deoxy-Hb ($\Delta C_{HB}$) and oxy-Hb ($\Delta C_{HBO_2}$). Change in oxygenation and blood volume or total hemoglobin (Hbt) may then be deduced using the following equation:

$$\text{Oxygenation} = \Delta C_{HBO_2} - \Delta C_{HB}$$

The percentage of deoxy-Hb concentration may then be calculated as a ratio of the deoxy-Hb to at least one of an oxy-Hb concentration, a baseline deoxy-Hb, or a total hemoglobin volume. In one example embodiment, the percentage of deoxy-Hb may be measured at a sample rate, such as a 2 Hz sample rate, and may be measured in real time.

At 830, the state of anesthesia may be determined. In one embodiment, a percentage and/or rate of change of the deoxy-Hb concentration may be correlated to determine the state of anesthesia. Anesthetics may have direct cerebral vasodilatory effects and may increase cerebral blood flow. Increases in cerebral blood flow are generally followed by increases in cerebral blood volume. The increases in cerebral blood volume may cause excessive amount of total hemoglobin (Hbt), oxy-Hb and deoxy-Hb during deep anesthesia and may be caused by a combination of the decrease in neuronal metabolic demand coupled with an increase in cerebral blood flow.

In one example embodiment, the decreases in percentage and/or rate of deoxy-Hb changes during deep anesthesia may be monitored and correlated to the cerebral metabolic rate (demand) suppression by the administered anesthetic agents. For example, as shown in FIG. 7, Deoxy-Hb concentration may indicate a changing state of anesthesia as light anesthesia may be associated with relatively less deoxy-Hb concentration than deep anesthesia. Additionally, a change, such as a decrease, in the percentage of deoxy-Hb may be an indication of changing levels of cortical activity, such as increased cortical activity, and/or an emergence from anesthesia. For example, deoxy-Hb averages may demonstrate a very slow rate of change in deep anesthesia, whereas this rate of change may be drastically increased when the patient emerges to wakefulness. Returning to FIG. 6, in one embodiment, cortical activity may correspond to at least one of a state of anesthesia, a transition between states of anesthesia, or a risk level that corresponds to an emergence from anesthesia.

In another example embodiment, the state of anesthesia may be determined by comparing the percentage of deoxy-Hb to the baseline deoxy-Hb. The baseline deoxy-Hb may indicate the deoxy-Hb concentration and/or ratio that may exist in a patient prior to the administration of anesthesia and may indicate the deoxy-Hb levels that correlate to a state of awareness. After anesthesia is administered, a deoxy-Hb percentage and/or rate may be calculated. The deoxy-Hb percentage and/or rate may then be compared to the baseline deoxy-Hb to determine the state of anesthesia. For example, a deoxy-Hb concentration that is higher than the baseline deoxy-Hb concentration may indicate that the state of anesthesia is deep or light state.

In one example embodiment, a state of anesthesia may be at described in terms intraoperative data that such as times of anesthetic induction, first surgical incision, and wound closure as well as administration of medication. In another example embodiment, a state of anesthesia may be described in terms of the desired amount of patient brain activity during a phase of a procedure. For example, the state of anesthesia may be the deep state of anesthesia defined as the four-minute time interval prior to wound closure, or the light state of anesthesia defined as the four-minute time interval prior to eye opening. The state of anesthesia may also be emergence state of anesthesia defined as any time interval where the anesthetic agents no longer prevent patient awareness.

At 835, an amount of an anesthetic to administer may be determined. In one embodiment, the amount of anesthesia may be determined according to the state of anesthesia. For example, if the state of anesthesia indicates patient awareness, an amount of an anesthetic may be administered prevent awareness. In another example embodiment, the levels of deoxy-Hb may be used to administer the minimal dose of anesthetic required to achieve the desired depth of anesthesia. For example, by monitoring the levels of deoxy-Hb, the effectiveness of anesthesia on a patient may be determined. Upon determining the effectiveness of anesthesia, a dosage of anesthesia may be provided to change the levels of deoxy-Hb and achieve the desired depth of anesthesia. The administration of anesthesia may include intravenous drug doses, such as Fentanyl, Propofol, or the like, and inhalational drugs, such as Sevoflurane, Desflurane, or the like.

FIG. 9 depicts a flow diagram of an example method for removing the effect of an artifact from an fNIR signal. The example method may be implemented using, for example, the device 20 and/or the computing device 220 of the system 10 described with respect to FIGS. 1-3. In an example embodiment, the method may take the form of program code (i.e., instructions) that may be executed by, for example, the capture device 20 and/or the computing environment 12 of the system 10 described with respect to FIG. 1-3.

According to an example embodiment, at 905, a 730 nm fNIR signal, an 850 nm fNIR signal, and reference fNIR signal may be received and/or acquired. The reference signal may be used to remove noise from the 730 nm and 850 nm fNIR signals that may be used to measure oxy-Hb and/or deoxy-Hb. For example, the reference signal may be emitted to capture non-cortical signals during a period of minimal activation. These non-cortical signals may then be used to calibrate and/or remove noise from the other emitted signals.

In another example embodiment, the 730 nm, the 850 nm, and the reference fNIR signals may be received at a location near the frontal cortex of the patient. For example, the fNIR signal may be emitted at or near a patient's scalp. The fNIR signal may pass through layers of tissue and may be absorbed and scattered by the oxy-Hb and deoxy-Hb. As shown in FIG. 5, a predictable quantity of fNIR signal may follow a banana-shaped path and leave the tissue.

Referring back to FIG. 9, at 910, a signal level and correlation check may be performed. Calculations for hemodynamic signals may be carried out using the measurements obtained for the 730 nm and 850 nm fNIR signal. In one embodiment, a signal level check may be performed to determine the signal strength of the 730 nm, 850 nm, and reference NIR light. If a weak signal is detected, an adjustment may be made to strengthen the signal.

At 915, a dark current measurement may be taken to determine whether a component analysis algorithm may be employed. A dark current measurement may be a measurement taken when NIR light is not being emitted. The dark current measurement may be used to determine whether non-cortical signals may be received. This may be done to ensure that component analysis may be performed when non-cortical signals may affect the fNIR signals.

At 920, in one example embodiment, a switching technique may be used to select the component analysis algorithm such as a principal component analysis (PCA), an independent component analysis (ICA), or the like. Artifacts signals may be identified and/or removed by capturing the non-cortical signal indicative of the artifact and removing the non-cortical signal from the fNIR using a component analysis algorithm. In selecting the component analysis algorithm, a switching technique may be used to select the component analysis algorithm that performs better.

For example, for each wavelength measurement either at 730 nm or 850 nm, a separate ICA and PCA algorithm may be performed where the measurement vector x(t) may be a two dimensional containing the measurement obtained either at 730 or at 850 nm and the one at the reference signal. The unknown independent/uncorrelated source signals s(t) that may be estimated by the ICA/PCA algorithm may also be two dimensional which will be the non-physiological noise signal and the clean raw intensity signal related with hemodynamic changes due to cognitive activity. Once the unknown A matrix and the unknown source signals s(t) are extracted, the noise signal may be selected by correlating the independent components with the reference signal separately and selecting the one analysis giving the highest correlation, such as a correlation above 0.7.

At 930, the selected component analysis algorithm may be applied to the 730 nm fNIR signal and/or the 850 nm fNIR signal.

At 935, the effect of an artifact may be removed from the fNIR signal and/or ignored. In one embodiment, the selected component analysis algorithm may be used to remove the effect of the artifact from the fNIR signal by subtracting a portion of the non-cortical signal from the fNIR signal. For example, after the independent component corresponding to the noise signal has been selected, the noise may be removed from the original 730 nm or 850 nm recordings by subtracting it from that measurement with an appropriate amount, such as the amount the estimated A matrix described previously. Correlation between the reference signal measurement and the noise removed intensity measurements via ICA and PCA algorithms are calculated separately. The outcome of the best performing algorithm that generates lowest correlation may be selected as the cleaned raw intensity measurement.

In one embodiment, a component analysis algorithm may not used. Non-cortical signals may not be detected in the 730 nm, 850 nm, or reference fNIR signals

What is claimed:

1. A method comprising:
   receiving a near-infrared signal in response to directing wavelengths of light in a near-infrared range on a patient;
   determining, from the near-infrared signal, a relative deoxyhemoglobin concentration and oxyhemoglobin concentration;
   analyzing the percentage of the deoxyhemoglobin concentration to determine a corresponding state of anesthesia; and
   administering an amount of anesthetic according to the corresponding state of anesthesia.

2. The method of claim 1, wherein the near-infrared signal is indicative of a change in the light at each of the wavelengths.

3. The method of claim 2, wherein the change in the light at each of the wavelengths is due to at least one of reflection or an absorption of the light by tissue of the patient.

4. The method of claim 2, further comprising measuring the change in the light at each of the wavelengths.

5. The method of claim 4, wherein the change measured in the light is at least one of an optical density change or a light intensity change.

6. The method of claim 1, further comprising determining a total hemoglobin volume.

7. The method of claim 1, wherein the percentage of the deoxyhemoglobin concentration is a ratio of the deoxyhemoglobin concentration to at least one of the oxyhemoglobin concentration, a baseline deoxyhemoglobin concentration, or a total hemoglobin volume.

8. The method of claim 1, wherein the analyzing comprises relating a change in the percentage of deoxyhemoglobin to a changing level of cortical activity.

9. The method of claim 1, wherein the analyzing comprises relating a decrease in the percentage of deoxyhemoglobin to a level of increased cortical activity.

10. The method of claim 1, wherein the analyzing comprises relating a change in the percentage of deoxyhemoglobin to a changing state of anesthesia.

11. The method of claim 1, further comprising measuring a rate of change in the percentage of deoxyhemoglobin by comparing the change in the light at each of the wavelengths at different times.

12. The method of claim 11, wherein the analyzing comprises relating the rate of change to a state of anesthesia.

13. The method of claim 12, wherein the analyzing comprises relating a slow rate of change in the deoxyhemoglobin to a deep state of anesthesia.

14. The method of claim 12, wherein the analyzing comprises relating the rate of change to a changing state of anesthesia.

15. The method of claim 11, wherein the change in the light at each of the wavelengths is measured at a sample rate of 2 Hz.

16. The method of claim 1, wherein the corresponding the state of anesthesia comprises at least one of a deep state, a light state, or an emergence from anesthesia.

17. The method of claim 1, wherein the analyzing comprises relating a decrease in the percentage of deoxyhemoglobin to an emergence from anesthesia.

18. The method of claim 17, wherein the emergence from anesthesia is not identifiable from visual observation of the patient.

19. The method of claim 1, wherein a baseline near-infrared signal is obtained prior to an administration of anesthesia indicative of a baseline deoxyhemoglobin percentage.

20. The method of claim 19, wherein determining the state of anesthesia comprises comparing the percentage of deoxyhemoglobin to the baseline deoxyhemoglobin percentage.

21. The method of claim 19, where the baseline near-infrared signal is obtained about 20 seconds before the administration of anesthesia.

22. The method of claim 19, wherein the baseline near-infrared signal is indicative of the baseline deoxyhemoglobin percentage is obtained on a patient-by-patient basis.

23. The method of claim 1, wherein the change in the light is measured in accordance with Beer-Lambert law.

24. The method of claim 1, wherein the wavelengths comprise two wavelengths of light, each in a range between 700 nm and 900 nm.

25. The method of claim 1, wherein a first wavelength is substantially absorbed by deoxyhemoglobin and a second wavelength is substantially absorbed by oxyhemoglobin.

26. The method of claim 25, wherein the first wavelength is 730 nm and the second wavelength is 850 nm.

27. The method of claim 1, further comprising directing the wavelengths of light in the near-infrared range on the patient.

28. The method of claim 27, wherein the near-infrared light is directed at a prefrontal cortex of the patient.

29. The method of claim 27, wherein the near-infrared light is directed to pass through human tissue.

30. The method of claim 27, wherein the wavelengths of light are directed on the patient after an administration of anesthesia.

31. The method of claim 1, wherein the amount of anesthetic to be administered is determined from the percentage of deoxyhemoglobin.

32. The method of claim 1, further comprising subtracting an effect of non-cortical signals on the near-infrared signal.

33. The method of claim 1, wherein the percentage of deoxyhemoglobin is measured in real-time.

34. The method of claim 1, further comprising comparing the percentage of deoxyhemoblogin concentration to a neuromarker that indicates a percentage of deoxyhemoglobin that corresponds to a level of cortical activity.

35. The method of claim 34, further comprising relating the level of cortical activity to at least one of the state of anesthesia, a transition between states of anesthesia, or a risk level that corresponds to an emergence from anesthesia.

36. A near-infrared device for determining a state of anesthesia, the device comprising:
a light detector for receiving a near-infrared signal indicative of a change in light in response to directing wavelengths of light on a patient; and
a processor for determining, from the near-infrared signal, a relative deoxyhemoglobin concentration and oxyhemoglobin concentration, and analyzing the percentage of the deoxyhemoglobin concentration to determine a corresponding state of anesthesia.

37. The device of claim 36, wherein the device comprises a flexible portion having the light detector affixed thereto.

38. The device of claim 37, wherein the flexible portion comprises a disposable material for attaching the flexible portion to the patient.

39. The device of claim 37, wherein the flexible portion is adapted for adapting to contours of a patient's head for maintaining the light detector in an orientation orthogonal to a surface of the patient's head.

40. The device of claim 37, wherein the flexible portion comprises a reusable circuit board for housing the light detector.

41. The device of claim 36, further comprising a light source for directing wavelengths of light in a near-infrared range.

42. The device of claim 41, wherein the light source has a peak wavelength of at least one of 730 nm, 805 nm, or 850 nm.

43. The device of claim 41, wherein the device comprises a flexible portion having the light source affixed thereto.

44. The device of claim 36, further comprising a data acquisition board for switching between a plurality of light sources.

45. The device of claim 36, further comprising a data acquisition board for switching between a plurality of light detectors.

46. The device of claim 36, wherein the deoxyhemoglobin concentration is relative to a baseline near-infrared signal recorded prior to an administration of an anesthetic.

47. The device of claim 46, wherein the processor executes computer-executable instructions for determining the deoxyhemoglobin concentration relative to the baseline, and analyzing the percentage of the deoxyhemoglobin concentration to determine the state of anesthesia.

48. The device of claim 36,
wherein the light detector captures a non-cortical signal, the non-cortical signal indicative of an artifact,
wherein the processor implements a switch algorithm to select between a principal component analysis (PCA) and an independent component analysis (ICA) noise removal algorithm to remove an effect of the artifact from the near-infrared signal by subtracting a portion of the non-cortical signal from the near-infrared signal.

* * * * *